United States Patent
Cao et al.

(10) Patent No.: US 11,852,806 B2
(45) Date of Patent: Dec. 26, 2023

(54) METHOD FOR CONTROLLING HYBRID SCANNING BASED ON MINIATURE REFLECTING DEVICE

(71) Applicant: BEIJING INSTITUTE OF TECHNOLOGY, Beijing (CN)

(72) Inventors: Jie Cao, Beijing (CN); Qun Hao, Beijing (CN); Guoliang Li, Beijing (CN); Mingyuan Tang, Beijing (CN); Chun Bao, Beijing (CN); Zixiong Wu, Beijing (CN)

(73) Assignee: BEIJING INSTITUTE OF TECHNOLOGY, Beijing (CN)

( * ) Notice: Subject to any disclaimer, the term of this patent is extended or adjusted under 35 U.S.C. 154(b) by 565 days.

(21) Appl. No.: 17/157,530

(22) Filed: Jan. 25, 2021

(65) Prior Publication Data
US 2021/0255455 A1 Aug. 19, 2021

(30) Foreign Application Priority Data
Feb. 13, 2020 (CN) .......................... 202010091134.4

(51) Int. Cl.
*G02B 26/10* (2006.01)
*A61B 5/00* (2006.01)
(Continued)

(52) U.S. Cl.
CPC .......... *G02B 26/101* (2013.01); *A61B 5/0064* (2013.01); *G02B 26/0833* (2013.01);
(Continued)

(58) Field of Classification Search
CPC .. G02B 26/101; G02B 26/0833; G02B 26/10; A61B 5/0064; A61B 2562/028; A61B 2576/00; A61B 5/0062; A61B 5/725; A61B 5/0079; A61B 2562/0233; G09G 3/025; H04N 9/3135
See application file for complete search history.

(56) References Cited

U.S. PATENT DOCUMENTS

| 2012/0307211 A1* | 12/2012 | Hofmann | G02B 26/101 353/31 |
| 2016/0238834 A1* | 8/2016 | Erlich | G02B 26/101 |
| 2018/0059221 A1* | 3/2018 | Slobodyanyuk | G01S 7/4814 |

* cited by examiner

*Primary Examiner* — Sahlu Okebato
(74) *Attorney, Agent, or Firm* — McClure, Qualey & Rodack, LLP (57) ABSTRACT

A method for controlling hybrid scanning based on a miniature reflecting device, which includes: loading parameters for determinant scanning and circular scanning, setting a scanning start point, and performing determinant scanning; performing low-pass filtering on received sampling data to filter an outlier in a sampling process, and performing singular value determining, to determine whether there is a valid connected domain within a scanning field of view; determining, as a target of interest, a valid connected domain with a maximum quantity of singular values, and obtaining a geometric center of the target of interest by calculating an average value of driving voltages corresponding to the singular values; performing circular scanning by using the geometric center as a scanning center, determining, in a process of scanning an outermost ring, whether singular values are centrosymmetrically distributed on the ring, to fine-tune the scanning center till the singular values are centrosymmetrically distributed on the ring.

5 Claims, 4 Drawing Sheets

(51) Int. Cl.
*G02B 26/08* (2006.01)
*H04N 9/31* (2006.01)
*G09G 3/02* (2006.01)

(52) U.S. Cl.
CPC ........... *G09G 3/025* (2013.01); *H04N 9/3135* (2013.01); *A61B 2562/028* (2013.01)

METHOD FOR CONTROLLING HYBRID SCANNING BASED ON MINIATURE REFLECTING DEVICE

TECHNICAL FIELD

The present disclosure relates to the photodetection field, and in particular, to a method for controlling hybrid scanning based on a miniature reflecting device.

BACKGROUND

A micro-electro-mechanical systems (MEMS) mirror is a miniature reflecting device incorporating an optical MEMS technology and integrating a micro-optical reflecting mirror and an MEMS drive. The MEMS mirror can move in translational and torsional modes. A torsional MEMS mirror is mainly used for laser alignment deflection, graphical scanning, image scanning, environmental perception, and the like. As an essential key laser component for laser application, an MEMS scanning mirror has been widely applied to consumer electronics, medical, military, national defense, communication, and other fields. At present, scanning mirrors can be mainly used for LiDARs, 3D cameras, barcode scanning, laser printers, medical imaging, and the like.

Currently, most MEMS scanning devices mainly support determinant scanning in an MEMS laser imaging technology. In image perception, determinant scanning provides even image resolutions, but makes it difficult to support a wide field of view and a high resolution at the same time. In view of this, some scholars put forward circular scanning that simulates human's eyes, to support the wide field of view and the high resolution at the same time. However, during circular scanning, a scanning center needs to be artificially determined, and this makes it difficult to further improve an imaging effect.

SUMMARY

The present disclosure discloses a method for controlling hybrid scanning based on a miniature reflecting device, to control hybrid scanning based on a miniature reflecting device (an MEMS scanning mirror), in other words, to support hybrid scanning of determinant scanning and circular scanning. Hybrid scanning supports scanning with a wide field of view and a high resolution. In addition, an automatic target positioning function is added to automatically determine a scanning center, and this improves an imaging effect.

The objective of the present disclosure is achieved by using the following technical solutions.

The method for controlling hybrid scanning based on a miniature reflecting device in the present disclosure includes: loading parameters for determinant scanning and circular scanning, setting a scanning start point, and performing determinant scanning; in a determinant scanning mode of an MEMS scanning mirror, performing low-pass filtering on received sampling data to filter an outlier in a sampling process, and performing singular value determining by calculating a quantity of singular values within a neighboring domain, to determine whether there is a valid connected domain within a scanning field of view; after completing determinant scanning, determining, as a target of interest, a valid connected domain with a maximum quantity of singular values, and obtaining a geometric center of the target of interest by calculating an average value of driving voltages corresponding to the singular values; and performing circular scanning by using the geometric center as a scanning center, determining, in a process of scanning an outermost ring, whether singular values are centrosymmetrically distributed on the ring, to fine-tune the scanning center till the singular values are centrosymmetrically distributed on the ring, performing circular scanning with a wide field of view and a high resolution based on the parameters specified for circular scanning, till the scanning is completed, and outputting a high-quality scanned image.

The method for controlling hybrid scanning based on a miniature reflecting device in the present disclosure includes the following steps:

Step 1: Load parameters for determinant scanning and circular scanning, and perform determinant scanning.

The step 1 is implemented as follows: loading the parameters for determinant scanning and circular scanning, where the parameters for determinant scanning include a quantity M1 of rows and a quantity N1 of columns, and the parameters for circular scanning include a quantity M2 of rings and a quantity N2 of points scanned on each ring; and setting a start point of determinant scanning to be at a maximum leftward and downward deflection angle of an MEMS scanning mirror, and performing determinant scanning, where the MEMS scanning mirror gradually deflects toward the right horizontally as a voltage applied to a pin X+ gradually increases.

Step 2: In a determinant scanning mode of the MEMS scanning mirror, perform low-pass filtering on received sampling data to filter an outlier in a sampling process, and perform singular value determining by calculating a quantity of singular values within a neighboring domain, to determine whether there is an object within a scanning field of view, in other words, to determine whether the domain is a valid connected domain.

Preferably, the step 2 is implemented as follows: in the determinant scanning mode of the MEMS scanning mirror, performing real-time Gaussian filtering on the received data by using a 3×3 Gaussian kernel shown in a formula (1); performing Gaussian low-pass filtering to filter the outlier, in the received data, due to a random error, and performing Gaussian blurring on the received data; comparing a depth threshold p with each of differences between neighboring sampling points in data obtained after Gaussian filtering; if a difference between neighboring sampling points is greater than the depth threshold p, determining that a next sampling value is a singular value; if a difference between the singular value and data collected within a 3×3 sampling point range centered on the singular value is not greater than a connected-domain threshold q, determining that the data is also a singular value, and starting a counter to calculate a quantity $\lambda$ of singular values in a connected domain; and if the counter displays that the quantity $\lambda$ of singular values is greater than a difference threshold $\tau$, determining that there is an object in the domain, and denoting the domain as the valid connected domain $\xi_n$.

$$\frac{1}{16}\begin{bmatrix} 1 & 2 & 1 \\ 2 & 4 & 2 \\ 1 & 2 & 1 \end{bmatrix} \quad (1)$$

Step 3: After completing determinant scanning, determine, as a target of interest, a valid connected domain with a maximum quantity of singular values, and obtain a geometric center of the target of interest by calculating an average value of driving voltages corresponding to the singular values.

The step 3 is implemented as follows: after completing determinant scanning, comparing quantities λ of singular values in valid connected domains $\xi_1, \xi_2, \xi_3, \ldots \xi_n$ that are obtained in the step 2, and selecting a valid connected domain with maximum λ as the target of interest; and using a formula (2) to calculate the average value of the voltages at sampling points corresponding to the singular values in the target of interest, where X and Y are deflection voltages required at the geometric center O of the target of interest;

$$X = \frac{x_1 + x_2 + \ldots x_{\lambda-1} + x_\lambda}{\lambda} \quad (2)$$
$$Y = \frac{y_1 + y_2 + \ldots y_{\lambda-1} + y_\lambda}{\lambda}$$

where $x_1, x_2, \ldots x_\lambda$ respectively represent driving voltages of the singular values in the target of interest at the pin X+, and $y_1, y_2, \ldots y_\lambda$ respectively represent driving voltages of the singular values in the target of interest at a pin Y+.

Step 4: Perform circular scanning by using the geometric center determined in the step 3 as a scanning center, determine, in a process of scanning an outermost ring, whether singular values are centrosymmetrically distributed on the ring, to fine-tune the scanning center till the singular values are centrosymmetrically distributed on the ring, perform circular scanning with a wide field of view and a high resolution based on the parameters specified for circular scanning in the step 1, till the scanning is completed, and output a high-quality scanned image.

The step 4 is implemented as follows: performing single-ring scanning by using M2 and N2 as scanning parameters, using the geometric center O of the target of interest as the scanning center, and using, as a deflection voltage of the outermost ring, a deflection voltage value of a sample point corresponding to a singular value farthest away from the scanning center in the valid connected domain in the determinant scanning mode; after completing scanning, determining whether singular value data is centrosymmetrically distributed on the scanned ring; if the singular value data is centrosymmetrically distributed on the scanned ring, performing global circular scanning by using the original scanning center as a scanning center and using M2 and N2 as scanning conditions; or if the singular value data is not centrosymmetrically distributed on the scanned ring, using the formula (2) to fine-tune the scanning center to further correct dynamic target positioning, and performing subsequent scanning by using a fine-tuned scanning center 02, M2, and N2 as scanning conditions, till the scanning is completed; and outputting the high-quality scanned image.

Beneficial Effects

1. Based on advantages of conventional determinant scanning and circular scanning, the method for controlling hybrid scanning based on a miniature reflecting device in the present disclosure supports scanning with the wide field of view and the high resolution while precisely determining the scanning center, and can be used to perform high-density scanning on a central field of view of the target of interest while monitoring a surrounding field of view.
2. According to the method for controlling hybrid scanning based on a miniature reflecting device in the present disclosure, in the process of determinant scanning, the sampling data is compared with the depth threshold, the connected-domain threshold, and the difference threshold in sequence to determine the target of interest. This can support a target positioning function.
3. According to the method for controlling hybrid scanning based on a miniature reflecting device in the present disclosure, the scanning center is fine-tuned by determining, in the process of scanning the outermost ring, whether the singular values are centrosymmetrically distributed on the ring, to further correct dynamic target positioning. This can further improve positioning accuracy of an MEMS scanning system in the circular scanning mode.

BRIEF DESCRIPTION OF DRAWINGS

In FIG. 3, 1 indicates a field programmable gate array (FPGA) development board, 2 indicates a laser driving device, 3 indicates a display screen, 4 indicates a laser, 5 indicates a drive unit of an MEMS galvanometer mirror, 6 indicates a reflecting mirror, 7 indicates the MEMS galvanometer mirror, 8 indicates an avalanche photodetector (APD) receiver, 9 indicates an APD drive unit, 10 indicates a power supplying unit, and 11 indicates a digital-to-analog conversion unit.

DETAILED DESCRIPTION

Specific implementations of the present disclosure are described below with reference to the accompanying drawings.

The present disclosure is further described below with reference to a hardware structure shown in FIG. 3.

Figure 3:
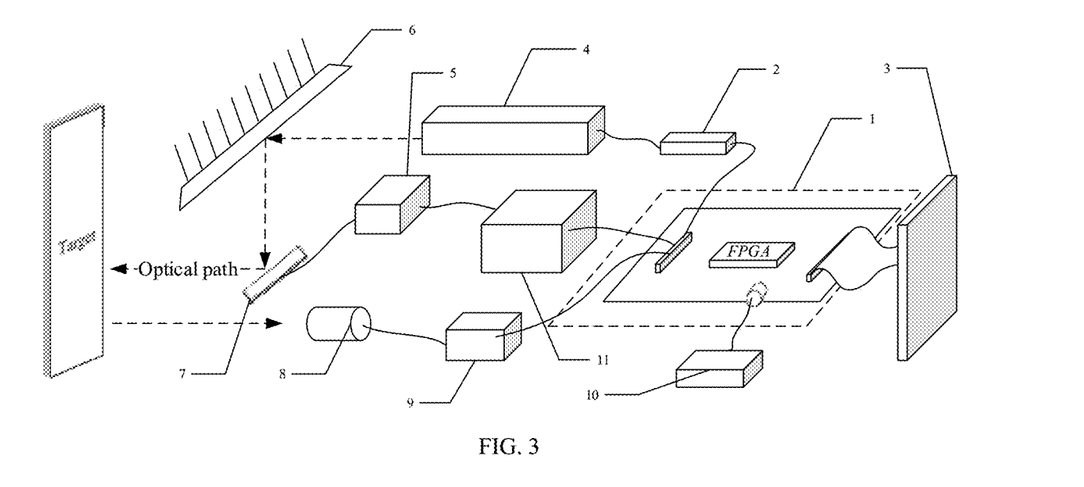
FIG. 3 is a schematic diagram of a hardware structure required in a running process in an embodiment of the present disclosure.

As shown in FIG. 3, the hardware structure required in a running process in the embodiments includes: an FPGA development board 1, a laser drive unit 2, a touchscreen 3, a laser 4, an MEMS drive unit 5, a reflecting mirror 6, an MEMS scanning mirror 7, an APD receiver 8, an APD drive unit 9, a storage unit 10, and a digital-to-analog conversion unit 11. A working process of hardware in the hardware structure is as follows: The FPGA development board 1 sends a start signal to the laser drive unit 2. The laser 4 emits laser light to the reflecting mirror 6, and the reflecting mirror 6 reflects the laser light to the MEMS scanning mirror 7. The MEMS scanning mirror 7 reflects the laser light to a front target. After being reflected by the front target, the laser light is received by the APD receiver 8 and stored in the storage unit 10. An image of the front target is displayed on the touchscreen 3 after received data is analyzed and processed. An algorithm in the present disclosure is embedded into the FPGA development board 1, and scanning parameters are input into a hardware system by using the touchscreen 3. The FPGA development board 1 outputs different levels to the digital-to-analog conversion unit 11. The digital-to-analog conversion unit 11 converts a digital level into an analog voltage, and sends the analog voltage to the MEMS drive unit 5. The MEMS scanning mirror 7 deflects with different poses to enable the laser light to scan the front target through different paths.

Figure 1:
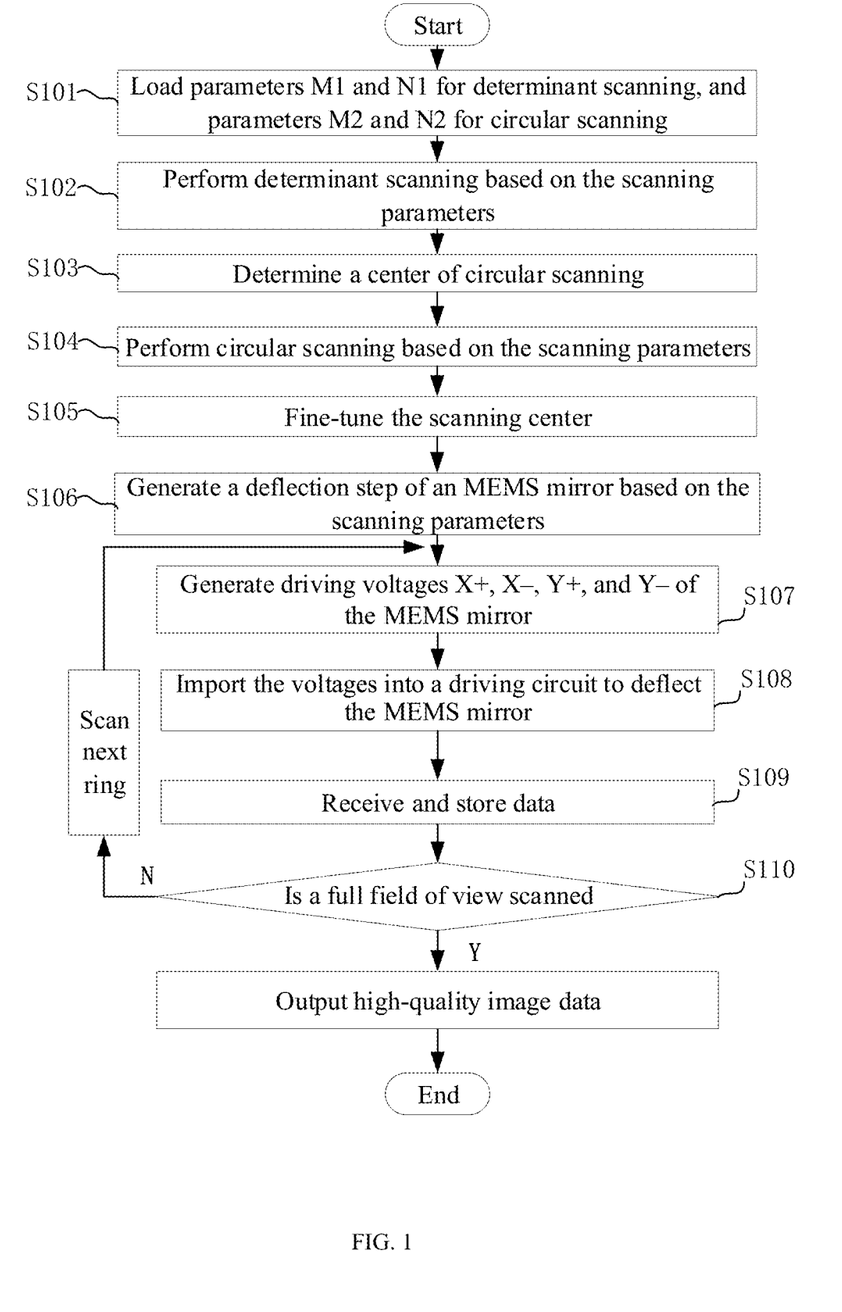
FIG. 1 is a flowchart of a method for controlling hybrid scanning based on miniature reflecting device in the present disclosure.
Figure 5:
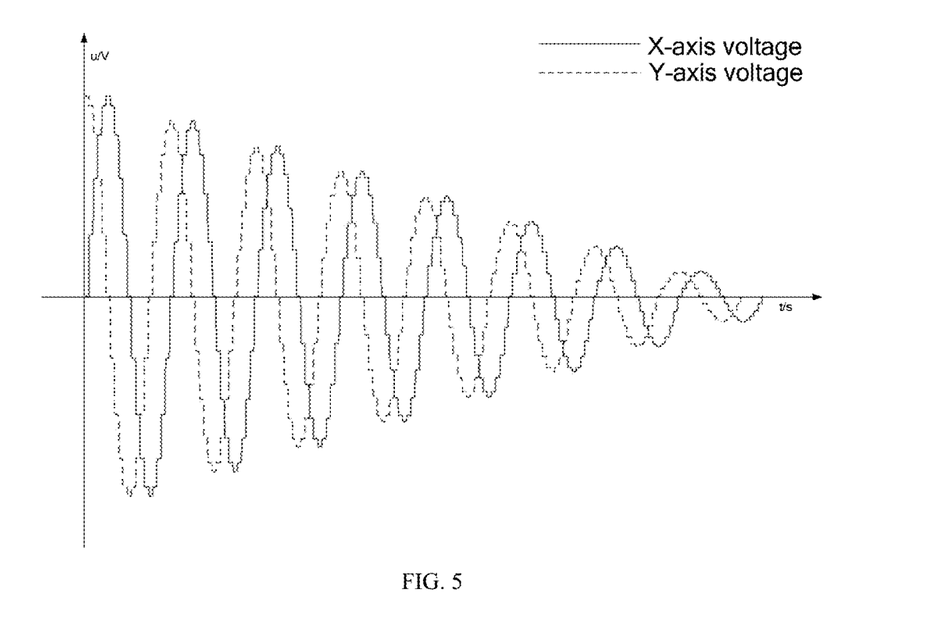
FIG. 5 shows a voltage oscillogram required for circular scanning in an embodiment of the present disclosure.
Figure 6:
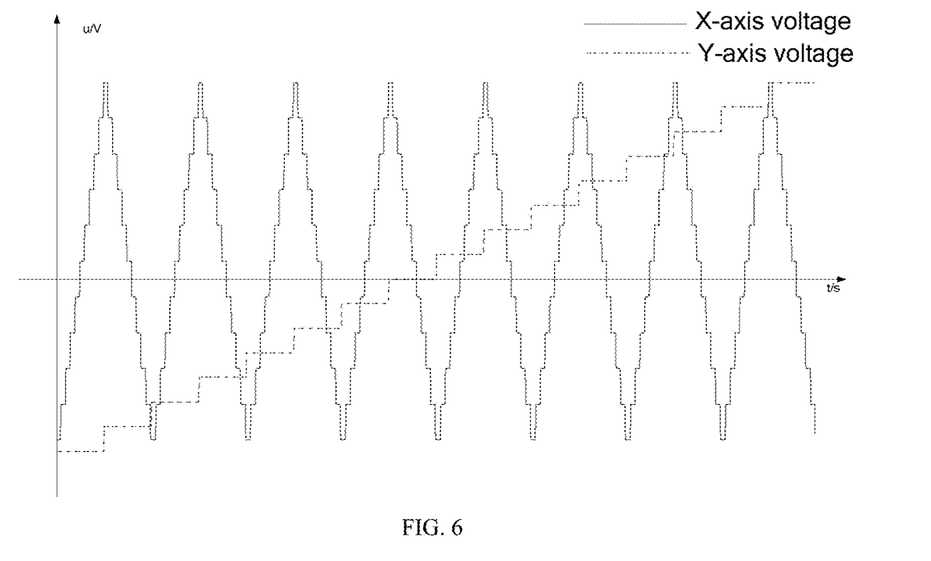
FIG. 6 shows a voltage oscillogram required for determinant scanning in an embodiment of the present disclosure.

FIG. 1 is a running flowchart of a method for controlling hybrid scanning based on a miniature reflecting device in the embodiments. Parameters for determinant scanning and circular scanning are input (S101) by using the touchscreen in the hardware structure shown in FIG. 3, and a scanning start point is set to perform determinant scanning. In addition, a start signal is sent to the laser drive unit in FIG. 3. Laser light emitted by the laser is reflected by the reflecting mirror to the MEMS scanning mirror. Then, the following steps are performed: performing (S102) determinant scanning, determining (S103) a center of circular scanning, performing (S104) circular scanning, fine-tuning (S105) the scanning center, generating (S106) a deflection step based on the parameters, and generating (S107) a driving voltage of the MEMS scanning mirror. The foregoing steps are all embodied in the algorithm in the FPGA development board in FIG. 3. Next, the generated driving voltage is imported (S108) into the MEMS drive unit to deflect the MEMS scanning mirror. Driving voltage waveforms for circular scanning and determinant scanning are shown in FIG. 5 and FIG. 6 respectively. The APD receiver and the storage unit in FIG. 3 receive and store (S109) data respectively. After scanning is completed for a full field of view, a scanned image is displayed on the touchscreen.

Figure 2:
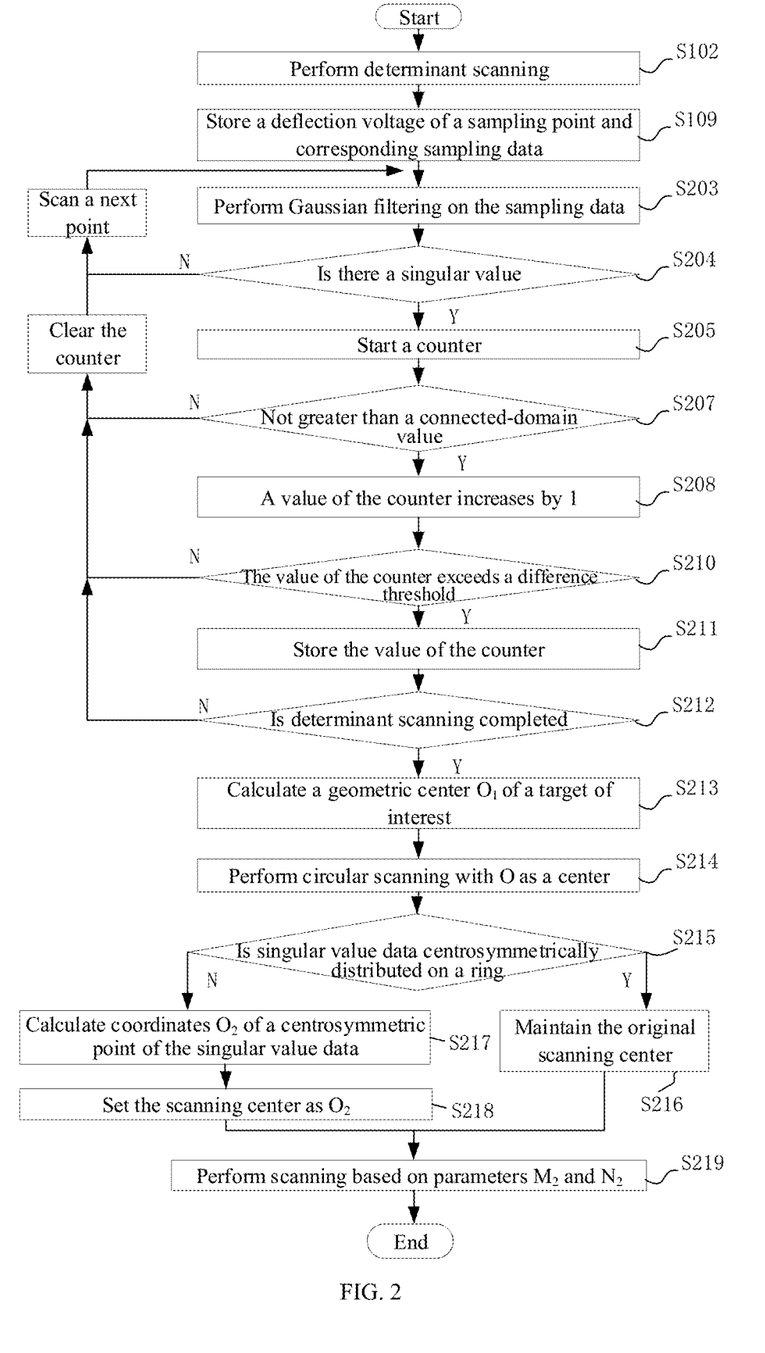
FIG. 2 is a flowchart of determining a target of interest in the present disclosure.

As shown in FIG. 1 and FIG. 2, the method for controlling hybrid scanning based on a miniature reflecting device in the embodiments is specifically implemented according to the following steps:

Step 1: Load the parameters for determinant scanning and circular scanning, and perform determinant scanning.

Figure 4A:
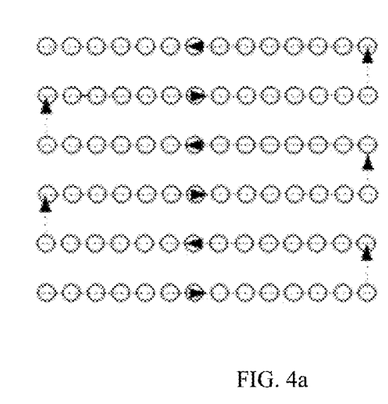
FIGS. 4a and 4b show schematic diagrams of circular scanning and determinant scanning in an embodiment of the present disclosure.

The step 1 is implemented as follows: loading the parameters for determinant scanning in which a front target is scanned row by row and parameters for a circular scanning in which the front target is scanned ring by ring around a same scanning center, where the parameters for determinant scanning include a quantity M1 of rows and a quantity N1 of columns, and the parameters for circular scanning include a quantity M2 of rings and a quantity N2 of points scanned on each ring; and setting the start point of determinant scanning to be at a maximum leftward and downward deflection angle of the MEMS scanning mirror, as shown in FIG. 4a, and performing determinant scanning, where the MEMS scanning mirror gradually deflects toward the right horizontally as a voltage applied to a pin X+ gradually increases.

Step 2: In a determinant scanning mode of the MEMS scanning mirror, perform low-pass filtering on received sampling data to filter an outlier in a sampling process, and perform singular value determining by calculating a quantity of singular values within a neighboring domain, to determine whether there is an object within a scanning field of view, in other words, to determine whether the domain is a valid connected domain.

The step 2 is implemented as follows: in the determinant scanning mode of the MEMS scanning mirror, performing (S203) real-time Gaussian filtering on the received data by using a 3×3 Gaussian kernel shown in a formula (1); performing Gaussian low-pass filtering to filter the outlier, in the received data, due to a random error, and performing Gaussian blurring on the received data; comparing a depth threshold p with each of differences between neighboring sampling points in data obtained after Gaussian filtering; if a difference between neighboring sampling points is greater than the depth threshold p, determining that a next sampling value is a singular value (S204), and starting (S205) a counter to calculate a quantity $\lambda$ of singular values in a connected domain; if a difference between the singular value and data collected within a 3×3 sampling point range centered on the singular value is not greater than a connected-domain threshold q (S207), determining that the data is also a singular value, and increasing (S208) a value of the counter by 1; and if the counter displays that the quantity $\lambda$ of singular values is greater than a difference threshold $\tau$ (S210), determining that there is an object in the domain, storing the value of the counter (S211), and denoting the domain as the valid connected domain $\xi_n$.

$$\frac{1}{16}\begin{bmatrix} 1 & 2 & 1 \\ 2 & 4 & 2 \\ 1 & 2 & 1 \end{bmatrix} \quad (1)$$

Step 3: After completing determinant scanning, determine, as a target of interest, a valid connected domain with a maximum quantity of singular values, and obtain a geometric center of the target of interest by calculating an average value of driving voltages corresponding to the singular values.

The step 3 is implemented as follows: after completing determinant scanning (S212), comparing quantities $\lambda$ of singular values in valid connected domains $\xi_1, \xi_2, \xi_3, \ldots \xi_n$ that are obtained in the step 2, and selecting a valid connected domain with maximum $\lambda$ as the target of interest; and using a formula (2) to calculate the average value of the voltages at sampling points corresponding to the singular values in the target of interest, where X and Y are deflection voltages required at the geometric center O of the target of interest (S213);

$$X = \frac{x_1 + x_2 + \ldots x_{\lambda-1} + x_\lambda}{\lambda} \quad (2)$$
$$Y = \frac{y_1 + y_2 + \ldots y_{\lambda-1} + y_\lambda}{\lambda}$$

where $x_1, x_2, \ldots x_\lambda$ respectively represent driving voltages of the singular values in the target of interest at the pin X+, and $y_1, y_2, \ldots y_\lambda$ respectively represent driving voltages of the singular values in the target of interest at a pin Y+.

Step 4: Perform circular scanning by using the geometric center determined in the step 3 as a scanning center (S214), determine, in a process of scanning an outermost ring, whether singular values are centrosymmetrically distributed on the ring (S215), and if not, to fine-tune (S217) the scanning center till the singular values are centrosymmetrically distributed on the ring (S218), and if so, to maintain (S216) the original scanning center; and perform (S219) circular scanning with a wide field of view and a high resolution based on the parameters specified for circular scanning in the step 1, till the scanning is completed, and output a high-quality scanned image.

Figure 4B:
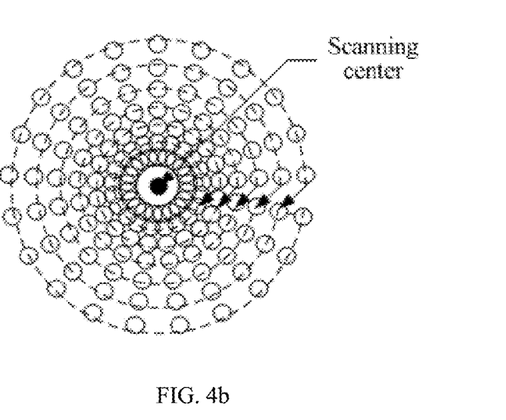

The step 4 is implemented as follows: performing circular scanning by using M2 and N2 as scanning parameters, and the geometric center O of the target of interest as the scanning center, where circular scanning is specifically performed from outside to inside, as shown in FIG. 4b; performing single-ring scanning by using, as a deflection voltage of the outermost ring, a deflection voltage value of a sample point corresponding to a singular value farthest away from the scanning center in the valid connected domain in the determinant scanning mode; after completing scanning, determining whether singular value data is centrosymmetrically distributed on the scanned ring; if the singular value data is centrosymmetrically distributed on the scanned ring, performing global circular scanning by using the original scanning center as a scanning center and using M2 and N2 as scanning conditions; or if the singular value data is not centrosymmetrically distributed on the scanned ring, using the formula (2) to fine-tune the scanning center to further correct dynamic target positioning, and performing subsequent scanning by using a fine-tuned scanning center 02, M2, and N2 as scanning conditions, till the scanning is completed; and outputting the high-quality scanned image.

The objectives, technical solutions, and beneficial effects of the present disclosure are further described in detail in the foregoing embodiments. It should be understood that the foregoing descriptions are merely specific embodiments of the present disclosure, but are not intended to limit the protection scope of the present disclosure. Any modification, equivalent replacement, improvement, or the like made within the spirit and principle of the present disclosure shall fall within the protection scope of the present disclosure.

What is claimed is:

1. A method for controlling hybrid scanning based on a miniature reflecting device, comprising the following steps:
    loading and determinant scanning step, configured for loading, into a memory device, parameters for determinant scanning in which a front target is scanned row by row and parameters for circular scanning in which the front target is scanned ring by ring around a same scanning center, and performing the determinant scanning by using a MEMS scanning mirror to reflect a laser light to a front target based on the parameters for determinant scanning;
    determining step configured for performing low-pass filtering on received sampling data in the determinant scanning to filter an outlier in a sampling process, and determining singular value by calculating a quantity of singular values within a neighboring domain, to determine whether there is an object within a scanning field of view, in other words, to determine whether the domain is a valid connected domain;
    obtaining step configured for after completing the determinant scanning, determining, as a target of interest, a valid connected domain with a maximum quantity of singular values, and obtaining a geometric center of the target of interest by calculating an average value of driving voltages corresponding to the singular values;
    circular scanning step configured for performing the circular scanning by using the geometric center as the scanning center, determining, in a process of scanning an outermost ring, whether singular values are centrosymmetrically distributed on the ring, to fine-tune the scanning center till the singular values are centrosymmetrically distributed on the ring, performing circular scanning with a wide field of view and a high resolution based on the parameters specified for circular scanning, till the scanning is completed, and outputting a high-quality scanned image.

2. The method for controlling hybrid scanning based on a miniature reflecting device according to claim 1, wherein the loading and determinant scanning step is implemented as follows: loading the parameters for determinant scanning and circular scanning, wherein the parameters for determinant scanning comprise a quantity M1 of rows and a quantity N1 of columns, and the parameters for circular scanning comprise a quantity M2 of rings and a quantity N2 of points scanned on each ring; and setting a start point of determinant scanning to be at a maximum leftward and downward deflection angle of the MEMS scanning mirror, and performing determinant scanning, wherein the MEMS scanning mirror gradually deflects toward the right horizontally as a voltage applied to a pin X+ gradually increases.

3. The method for controlling hybrid scanning based on a miniature reflecting device according to claim 2, wherein the determining step is implemented as follows: in the determinant scanning mode of the MEMS scanning mirror, performing real-time Gaussian filtering on the received data by using a 3×3 Gaussian kernel shown in a formula (1); performing Gaussian low-pass filtering to filter the outlier, in the received data, due to a random error, and performing Gaussian blurring on the received data; comparing a depth threshold p with each of differences between neighboring sampling points in data obtained after Gaussian filtering; if a difference between neighboring sampling points is greater than the depth threshold p, determining that a next sampling value is a singular value; if a difference between the singular value and data collected within a 3×3 sampling point range centered on the singular value is not greater than a connected-domain threshold q, determining that the data is also a singular value, and starting a counter to calculate a quantity $\lambda$ of singular values in a connected domain; and if the counter displays that the quantity $\lambda$ of singular values is greater than a difference threshold $\tau$, determining that there is an object in the domain, and denoting the domain as the valid connected domain $\xi_n$ $$\frac{1}{16}\begin{bmatrix} 1 & 2 & 1 \\ 2 & 4 & 2 \\ 1 & 2 & 1 \end{bmatrix} \quad (5)$$

4. The method for controlling hybrid scanning based on a miniature reflecting device according to claim 3, wherein the obtaining step is implemented as follows: after completing determinant scanning, comparing quantities $\lambda$ of singular values in valid connected domains $\xi_1, \xi_2, \xi_3, \ldots \xi_n$ that are obtained in the determining step, and selecting a valid connected domain with maximum $\lambda$ as the target of interest; and using a formula (2) to calculate the average value of the voltages at sampling points corresponding to the singular values in the target of interest, wherein X and Y are deflection voltages required at the geometric center O of the target of interest:

$$X = \frac{x_1 + x_2 + \ldots x_{\lambda-1} + x_\lambda}{\lambda} \quad (6)$$

$$Y = \frac{y_1 + y_2 + \ldots y_{\lambda-1} + y_\lambda}{\lambda}$$

wherein $x_1, x_2, \ldots x_\lambda$ respectively represent driving voltages of the singular values in the target of interest at the pin X+, and $y_1, y_2, \ldots y_\lambda$ respectively represent driving voltages of the singular values in the target of interest at a pin Y+.

5. The method for controlling hybrid scanning based on a miniature reflecting device according to claim 4, wherein the circular scanning step is implemented as follows: performing single-ring scanning by using M2 and N2 as scanning parameters, using the geometric center O of the target of interest as the scanning center, and using, as a deflection voltage of the outermost ring, a deflection voltage value of a sample point corresponding to a singular value farthest away from the scanning center in the valid connected domain in the determinant scanning mode; after completing scanning, determining whether singular value data is centrosymmetrically distributed on the scanned ring; if the singular value data is centrosymmetrically distributed on the scanned ring, performing global circular scanning by using the original scanning center as a scanning center and using M2 and N2 as scanning conditions; or if the singular value data is not centrosymmetrically distributed on the scanned ring, using the formula (2) to fine-tune the scanning center to further correct dynamic target positioning, and performing subsequent scanning by using a fine-tuned scanning center 02, M2, and N2 as scanning conditions, till the scanning is completed; and outputting the high-quality scanned image.

\* \* \* \* \*